(12) United States Patent
Theeuwes et al.

(10) Patent No.: US 7,371,229 B2
(45) Date of Patent: May 13, 2008

(54) DUAL ELECTRODE ADVANCED ELECTROCHEMICAL DELIVERY SYSTEM

(76) Inventors: Felix Theeuwes, 27350 Altamont Rd., Los Altos, CA (US) 94022; Jeremy Corwin Wright, 631 Questa Dr., Los Altos, CA (US) 94024; Stahinja K. Zecevic, 5517 Shady Maple Cove, Salt Lake City, UT (US) 84117

( * ) Notice: Subject to any disclaimer, the term of this patent is extended or adjusted under 35 U.S.C. 154(b) by 656 days.

(21) Appl. No.: 10/353,769

(22) Filed: Jan. 28, 2003

(65) Prior Publication Data
US 2004/0147907 A1 Jul. 29, 2004

(51) Int. Cl.
*A61K 9/22* (2006.01)
(52) U.S. Cl. .................................. 604/892.1
(58) Field of Classification Search ............. 604/892.1, 604/891.1, 890.1, 20, 132, 142, 290; 205/743; 204/252
See application file for complete search history.

(56) References Cited

U.S. PATENT DOCUMENTS

| 4,886,514 A | * | 12/1989 | Maget | ...................... 604/891.1 |
| 4,902,278 A | | 2/1990 | Maget et al. | |
| 6,120,665 A | | 9/2000 | Chiang et al. | |
| 6,289,241 B1 | * | 9/2001 | Phipps | ........................ 604/20 |
| 2002/0175191 A1 | * | 11/2002 | Joshi et al. | .................. 222/386 |
| 2003/0205582 A1 | * | 11/2003 | Joshi et al. | .................. 222/100 |

FOREIGN PATENT DOCUMENTS

WO    WO 01/01957    1/2001

* cited by examiner

*Primary Examiner*—Nicholas D. Lucchesi
*Assistant Examiner*—Christopher D Koharski
(74) *Attorney, Agent, or Firm*—David Fonda

(57) ABSTRACT

The present invention is disclosed herein as an electrochemical cell having a cell housing with a first half cell and a second half cell, and an ion selective membrane between the cells. The electrochemical cell further has a first electrode positioned within the first half cell, a second electrode positioned within the second half cell, an electrolyte in electrical communication with both the first electrode and the second electrode. The electrodes of the cell are configured so that the electrochemical cell maintains a substantially constant salt concentration level throughout operation. The cell is preferably used in conjunction with an implantable fluid delivery apparatus. A method for using the device is additionally disclosed.

36 Claims, 2 Drawing Sheets

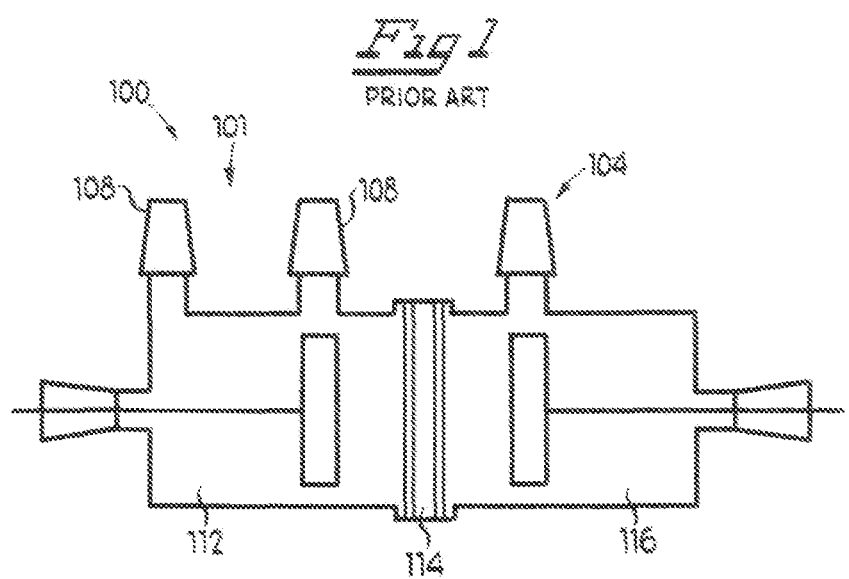
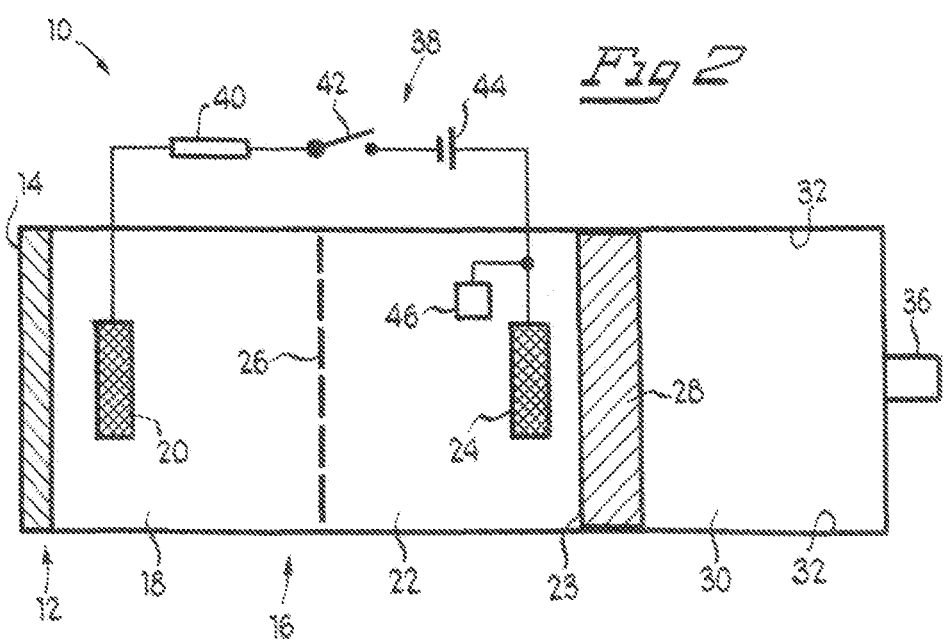

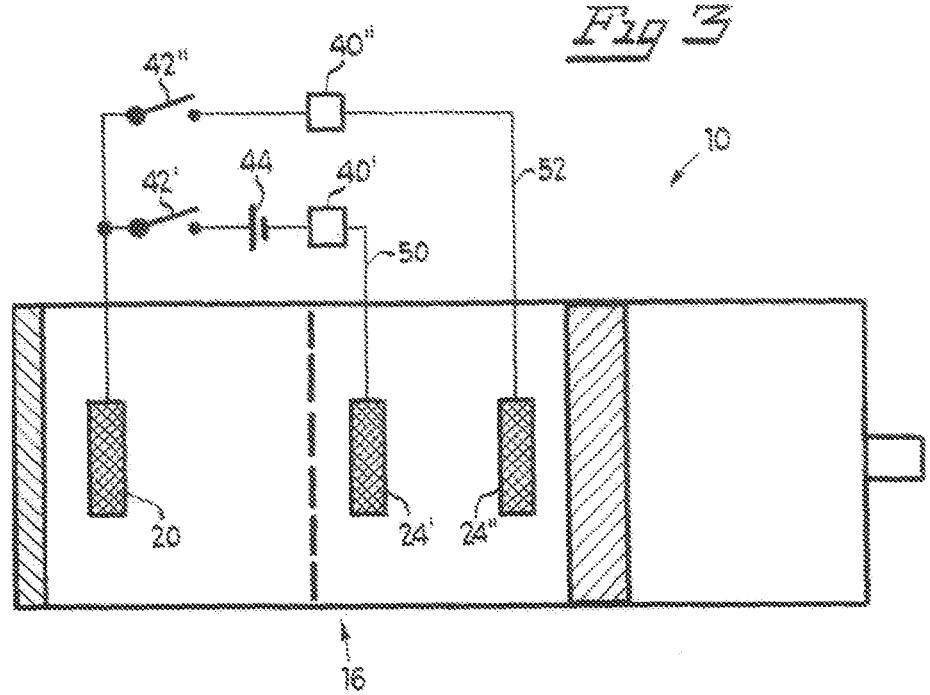
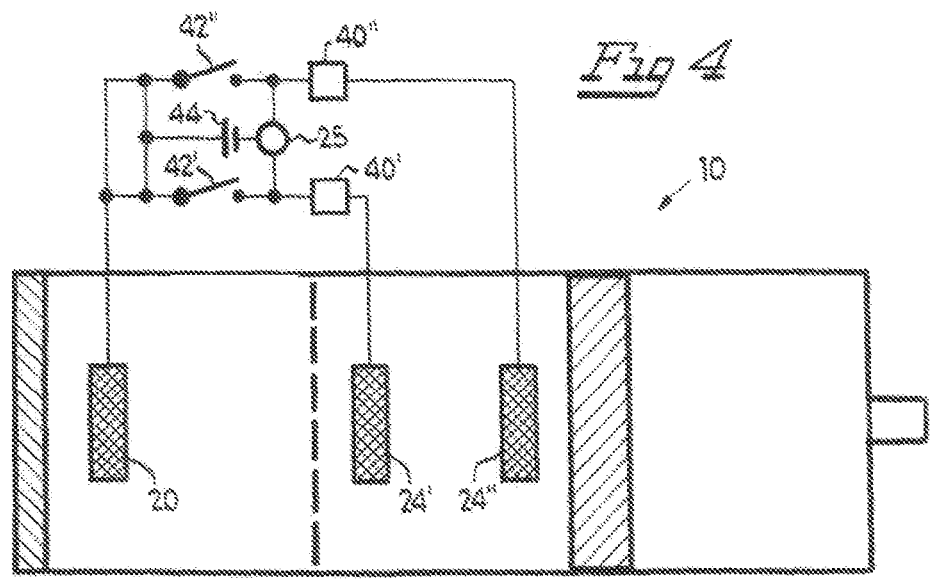

DUAL ELECTRODE ADVANCED ELECTROCHEMICAL DELIVERY SYSTEM

BACKGROUND OF THE INVENTION

1. Field of the Invention

The present invention is drawn generally to electrochemical fluid delivery devices, and specifically to an improved electro-osmotic fluid delivery system.

2. State of the Prior Art

Fluid delivery devices are well known in the art, ranging from pressurized fluid delivery, to mechanical fluid delivery, to electrochemical fluid delivery devices and beyond. One particularly interesting fluid delivery system is an electro-osmotic cell coupled with a delivery pump, forming an electro-osmotic pump. These simple pumps operate through the combination of an electrochemical cell and an ion-selective membrane to create a driving force for fluid delivery.

Conventional electro-osmotic pumps, however, have a number of problems that have not, as of yet, been addressed in the prior art. One particular problem has occurred in constant fluid delivery applications. As the operation of the device is continued over a period of time, it has been observed that the delivery rate is inconsistent, even though the current rate between the anode and the cathode is maintained at a constant rate. Generally, two types of osmosis are occurring with an electro-osmotic cell simultaneously. The primary and most prevalent type of osmosis is electro-osmosis, whereby charged ions (dissociated salts) are driven across an ion exchange membrane as the cell is operated, thereby dragging water molecules with them. The secondary and less prevalent form of transport is osmosis due to environmental conditions. Osmosis is the transfer of a solvent across a barrier, generally from an area of lesser solute concentration to an area of greater solute concentration. Given normal cell operating conditions, the environmentally-driven osmosis is negligible in comparison to the electro-osmosis.

As the relative concentrations of salts within the half cells of an electro-osmotic delivery device change, however, significant changes in the amount of fluid delivered have been observed. It has been postulated that as operation of the device is continued, the passage of ions (salts) across the membrane of the device causes an increase in the salt concentration within one of the half-cells. Eventually, the concentration becomes so high that a significant environmental osmosis flux develops. Thus, environmental osmosis becomes more prevalent, and affects the predictability and reliability of the cell operations. The additional solvent transfer causes an increase in the overall fluid amount contained in the one half-cell, increasing the rate of delivery of fluid.

The above-described effect can continue even after the operation of the cell has stopped. Even though the anode and the cathode are removed from electrical communication with one another, the concentration difference between the half-cells remains. Thus, additional solvent will continue to be pulled across the membrane, causing the fluid delivery device to continue delivering fluid even after the cell has ceased operation. This additional fluid delivery is termed "zero-current transport," and is deemed unacceptable—especially for long term use of a constant-rate fluid delivery device.

It is thus an object of the present invention to provide an improved cell design wherein the concentration differences between the half-cells within the device are avoided.

It is another object of the present invention to increase the reliability and consistency of the delivery rate of the device.

It is a further object of the present invention to eliminate, or substantially reduce, unwanted zero-current transfer.

These and other objects will become apparent to one of ordinary skill in the art in light of the present specification, claims and drawings appended hereto.

SUMMARY OF THE INVENTION

The present invention is disclosed herein as an electrochemical cell having a first half cell with a first electrode therein, a second half cell with a second electrode therein, and an ion exchange membrane therebetween. The electrochemical cell additionally has an electrolyte in electrical communication with both the first electrode and the second electrode, enabling operation of the cell. Further, the electrochemical cell additionally includes means for maintaining a substantially constant concentration of salts within the electrochemical cell. By maintaining a substantially constant salt concentration within the cell a large disparity in concentration differences between the first and second half cells can be avoided, and, therefore, irregularities in electro-osmotic transfer, as well as the presence of zero-current transfer, can be avoided.

In a preferred embodiment, the electrodes are constructed from substantially the same active materials, so that, during operation of the device, the ions created by one electrode are reacted with the opposing electrode. This, in turn, provides means for, and helps to maintain a substantially constant salt concentration within the electrochemical cell.

In a preferred embodiment, the first electrode and second electrode are both silver/silver chloride electrodes.

In order to regulate the operation of the electrochemical cell, the electrochemical cell preferably includes means for controlling the electrochemical cell. The controlling means can comprise a resistor, a complicated control circuit, or the like. These devices help to control the time course and magnitude of current that flows through the electrodes of the electrochemical cell. In a preferred embodiment, the electrochemical cell includes two or more second electrodes, wherein at least one of the two second electrodes comprise substantially the same active material as the first electrode. Preferably, the controlling means directs the flow of electricity between the first electrode and at least one of the two or more second electrodes. The flow of current may be directed either by splitting the current between the two second electrodes, or cycling the flow of current between the electrodes, as may be needed. In order to facilitate the simultaneous operation of the at least two second electrodes, it is preferred that the wiring loops for each electrode include a resistor, wherein the resistance value of one resistor is at least ten times greater than the resistance value of the other resistor.

The electrochemical cell may additionally includes an ionic sensor for measuring the ionic concentration of at least one of the two half cells. This concentration can then be used to determine the operation of the controlling means. Thus, the ionic sensor also serves as a means for maintaining a substantially constant salt concentration throughout the electrochemical cell.

In a preferred embodiment of the invention, the above electrochemical cell is incorporated into an electrochemical fluid delivery device. The fluid delivery device includes a fluid inlet, the above described electrochemical cell in fluid communication with the fluid inlet, a piston member or a movable partition adjacent the electrochemical cell, and a drug reservoir adjacent the piston member/movable partition, wherein the drug reservoir has an exit port. The electro-osmotic cell operates to steadily and consistently to deliver fluid from the drug reservoir until operations are halted. Throughout the operation of the device, the electrodes serve as means for, and help to maintain a substantially constant salt concentration level within the cell, which, in turn, ensures that environmental osmosis is minimized, increasing the reliability, predictability, and consistency of the delivery of fluid from the device, as well as ensuring that zero-current transport is minimized after cell operations have been stopped.

Preferably, the fluid inlet of the fluid delivery device is an osmotic membrane, and the electrolyte used within the device is a bodily fluid or a fluid that is isotonic with the body.

BRIEF DESCRIPTION OF THE DRAWINGS

FIG. 1 of the drawings depicts a cut-away side view of prior-art electrochemical fluid delivery device;

FIG. 2 of the drawings shows a cut-away side view of the fluid delivery device of the present invention; and FIG. 3 of the drawings shows a cut-away side view of an alternative embodiment of the fluid delivery device of the present invention.

FIG. 4 of the drawings shows a cut-away side view of an alternative embodiment of the fluid delivery device of the present invention.

DETAILED DESCRIPTION OF THE INVENTION

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

A prior art electrochemical device 100 comprising an electro-osmotic pump is shown in FIG. 1 as including fluid inlet 101, electro-osmotic (or electrochemical) cell 102, and fluid outlet 104. The fluid inlet 101 is shown as a pair of fluid conduits 108, which provide and then return a fresh supply of saline to cell 102, as needed. The electro-osmotic cell 102 is typically made up of a first half-cell 112, membrane 114, and second half-cell 115. Conventional devices such as the one shown in FIG. 1 typically operate by introducing a fluid into first half-cell 112, and pumping a portion of the fluid through membrane 114 by the electrochemical transfer of an ion across membrane 114. The fluid introduced into second half-cell 115 accumulates, delivering a fluid contained within second half cell 115 out of cell 102 via fluid outlet 104.

Typically, such prior art electro-osmotic devices, which may be used in fluid delivery systems, have a number of drawbacks. Although such devices are effective in delivering fluid through electro-osmotic transport, the consistency and predictability of fluid delivery can be affected through osmotic transport during and after cessation of the operation of the device (e.g., after current flow has ceased). During operation of the cell, conventional cells see an increase in the salt concentration within the cell itself. The salt concentration increase can affect cell operations, and, in particular, acts as a driving force for unwanted osmotic transport within the cell. This effect can even extend beyond cessation of electro-osmotic transport, causing osmotic transport even after cell current has been cut off. This type of post-operational osmotic transport is termed as zero-current transport.

Fluid delivery device 10 of the present invention helps to overcome these problems, among others. Fluid delivery device 10 is shown in FIG. 2 as comprising fluid inlet 14, electrochemical cell 16, piston 28, reservoir 30, exit port 36 and wiring apparatus 38. Fluid delivery device 10 is capable of, during operation, receiving fluid from an external source through fluid inlet 14 into electrochemical cell 16, pumping that fluid through cell 16 towards piston 28 to, in turn, displace piston 28 into reservoir 30, delivering fluid out of reservoir 30 and through exit port 36. As will be explained, fluid delivery device 10 is capable of delivering a steady flow of fluid at predictable, determinable rates over a long period of time. In a preferred embodiment, reservoir 30 contains a drug formulation and fluid delivery device 10 operates to deliver drug at a controlled rate.

Fluid delivery device 10 is shown in FIG. 2 as generally comprising an elongated cylindrical shaped device. The teachings of the present invention may be utilized with a wide variety of fluid-delivery devices, ranging from extremely large industrial delivery processes to micropumps. One particularly useful application for the present pump technology is in implantable medical pumps. These pumps are implanted within patients for the delivery of medicament to a patient over a long period of time. The teachings of the present invention will be discussed relative to such an implantable device, and will be shown within such an environment. Although fluid delivery device 10 is shown in conjunction with the implantable devices, it should be noted that the teachings contained within this specification and the appended claims may be translated to other devices and applications without straying from the intended scope of this disclosure.

Fluid inlet 14 of device 10 is shown in FIG. 2 as generally comprising a membrane associated with an end portion 12 of device 10. Preferably, device 10 is associated with a water-rich environment so that, during operation, water may be allowed into cell 16 through inlet 14. Alternatively, and as shown in FIG. 1, fluid inlet 14 could comprise one or more conduits 51 for the delivery of a fluid into cell 16. In any case, fluid inlet 14 should provide a constant and ready supply of fluid for electro-osmotic cell 16 so as to ensure ongoing and consistent operation.

Electro-osmotic cell 16 is shown in FIG. 2 as comprising first half-cell 18 and second half-cell 22, with membrane 26 in-between. Fluid inlet 14 is shown associated with first half-cell 18, allowing fluid from the surrounding environment of device 10 into cell 16. Within first half-cell 18 and second half-cell 22 are electrodes, shown in FIG. 1 with first electrode 20 in first half-cell 18, and second electrode 24 in second half-cell 22. First 20 and second 24 electrodes preferably comprise a cathode and an anode, respectively. Also, generally first 18 and second 22 half-cells are named with the particular electrode type contained therein, and as such will hereafter be called cathode half-cell 18 and anode half-cell 22.

In order to optimize operation of the cell, and to ensure that the occurrence of osmotic transfer (non-electro-osmotic) both during and after operation is minimized, both the anode 24 and the cathode 20 may be constructed from the same active materials. For example, in one preferred embodiment, both the cathode 20 and anode 24 could comprise an Ag/AgCl electrode. In this case, the cathode would undergo the following reaction in operation:

Equation 1

And the anode would undergo the following reaction:

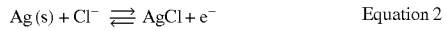

Equation 2

As can be seen from the above equations, in a preferred embodiment the cathode produces a chloride ion, which is then passed across the membrane to the anode half-cell, whereafter the anode recomplexes the chloride ion into insoluble silver chloride, which then precipitates out of solution. In doing so, the concentration of the salt, namely the chloride ion, does not increase during operation, as it is complexed out of solution continuously. In addition, water is also transported with the chloride ions when current is flowing, resulting in a net volume flux into second half cell 22, and therefore fluid delivery from reservoir 30.

Although the above embodiment solely describes the use of silver/silver-chloride active material electrodes, any other number of active materials could be similarly be available for use as electrodes. As would be understood by one of ordinary skill in the art, simple experimentation could produce numerous other active materials for use in the present invention provided the electrodes serve as means for, and maintain a substantially constant salt concentration within the cell during operation. Without intending to limit this invention, examples of other electrode systems include:

| Anode | Cathode |
|---|---|
| $Hg/Hg_2Cl_2$ | $Hg/Hg_2Cl_2$ |
| $Ag/AgBr$ | $Ag/AgBr$ |
| $Ag/AgC_2O_4$ | $Ag/AgC_2O_4$ |
| $Ag/Ag_2SO_4$ | $Ag/Ag_2SO_4$ |
| $AgO/Ag_2O$ | $AgO/Ag_2O$ |
| $NiOOH/Ni(OH)_2$ | $NiOOH/Ni(OH)_2$ |
| $Fe/Fe(OH)_2$ | $Fe/Fe(OH)_2$ |
| $Zn/Zn(OH)_2$ | $Zn/Zn(OH)_2$ |
| $Fe/Fe(OH)_2$ | $NiOOH/Ni(OH)_2$ |
| $Zn/Zn(OH)_2$ | $AgO/Ag_2O$ |

Regardless of the particular material selected for use, the ion that is passed across the membrane 26 may be neutralized in a variety of ways. Generally, it is preferred that the ion that is passed across membrane 26 is thereafter complexed with either an ion that is already present on the other side of membrane 26, or with another ion like itself in a catalyzed self-neutralizing reaction. Additionally, the ion could react with the opposing electrode, complexing and plating on that electrode, or precipitating out of the electrolyte. These materials and the reactions involving the passing ion serve as means for maintaining a substantially constant salt concentration within the electrochemical cell during operation of same. As these reactions proceed, the ionic concentration of the solution contained within anode half-cell 22 will be maintained substantially constant.

Membrane 26 of cell 16 generally comprises an ion-selective membrane that allows the passage of the ions produced at cathode 20, while substantially maintaining the integrity between cathode half-cell 18 and anode half-cell 22. Usually, membrane 26 is selective for the passage of either anions or cations (but not both). The particular material selected for membrane 26 is dictated by the electrode materials selected and the desired pumping rate of device 10. Typical materials, however, include AM-1, AM-3, AFN and AMX from Ameridia; Nafion from Dupont; CMI 7000 C/R from Membranes International and others known to the art.

The teachings associated with the electro-osmotic cell 16 of the present device do not necessarily need to be limited to fluid-delivery devices. Applications for the extended use and consistent operation of the cell 16 of the present invention can extend beyond the fluid delivery art, to and including controlled release of any substance in manner that is minimally affected by temperature or pressure. Thus, although the present disclosure is shown in conjunction with a fluid-delivery device, it may be possible to transplant the teachings of the electrochemical cell into another device, as mentioned above, without parting from the scope of this disclosure.

In order to translate the net volume change of fluid from first half cell 18 into second half cell 22, fluid delivery device 10 includes a movable partition, movable wall, piston, or other similar structure which moves to expand the volume of second half cell 22 upon a sufficient increase in cell volume. For clarity and simplicity, such a movable structure will generally be referred to as piston 28, without intending to limit the device to that structure specifically. Piston 28 is associated with the distal end 23 of anode half-cell 22, sealing off that portion of device 10 from drug reservoir 30. Piston 28 is slideably associated within device 10 so that, as the volume of fluid contained within anode half-cell 22 increases or decreases, piston 28 is correspondingly maneuvered into and out of drug reservoir 30. From this process, fluid contained within drug reservoir 30 can be pushed out for delivery, or drawn in if device 10 operation so dictates. Other structures could similarly be utilized to perform the same functional task with an alternative structure. For example, piston 28 could comprise a diaphragm, or another similar structure that is capable of conveying an increase in pressure or volume from one compartment to another, while maintaining the integrity of each compartment.

Exit port 36 preferably comprises an open aperture between the reservoir 30 and the surrounding environment. Although not shown, exit port 36 may additionally include any number of fluid-delivery control devices such as nozzles, valves, or other control devices for regulating flow rate of fluid out of device 10. In its simplest and most preferred form, however, exit port 36 is merely a static aperture, and control rate of fluid out of reservoir 30 is dictated entirely by operation of electro-osmotic cell 16.

Wiring apparatus 38 is shown in FIG. 2 as comprising power source 44, switch 42, and means 40 for controlling the electrochemical cell, which together help to control the rate of delivery of fluid out of exit port 36. Together, power source 44, switch 42 and controlling means 40 provide a control mechanism for cell 16, regulating the rate of operation as well as timing of beginning and ending of operation. Controlling means 40 may comprise a simple resistor within the circuit, or may comprise a more sophisticated mechanism such as a computerized control circuit, which regulates the flow of electricity through anode 24 and cathode 20 electrodes. Controlling means 40 may be powered by power source 44 so that, once switch 42 is closed (the operation of which may be controlled by controlling means 40), operation of device 10 is commenced according to the instructions of controlling means 40. Alternatively, controlling means 40 could comprise power source 44 itself, with the operational voltage of power source 44 regulating at least one of the magnitude and time course of the current through that loop.

Controlling means 40 may additionally comprise sensor 46. Sensor 46 is situated in the wall of anode half-cell 22 of cell 16 such that it is in direct contact with the solution contained therein. Sensor 46 is capable of detecting the conductivity of the fluid in half cell 22 or the concentration of any number of ionic species contained within anode half-cell 22, but especially should be able to detect and measure the ionic concentration of the ion produced by cathode 20 during operation and thereby together with the electrode configuration serve as means for maintaining a substantial salt concentration within the electrochemical cell during operation of the electrochemical cell. Typical sensors include conductivity sensors, sodium ion sensors, Ag/AgCl chloride ion sensor, etc. By monitoring the conductivity or ionic concentration of anode half-cell 22, control member 40 may regulate the operation of electro-osmotic cell 16 so as to maintain a consistent and predictable flow rate out of device 10.

In operation, fluid delivery device 10 is first placed or implanted into a moisture-rich environment such as a human being. Once in place, fluid delivery device 10 is configured for operation by manipulating wiring apparatus 38 into final operative position. This can be done, for example, by simply closing switch 42, or by programming controlling means 40 to begin cell 16 operations.

After operation has begun, fluid is allowed into cell 16 via fluid inlet 14. Fluid enters into cathode half-cell 18 of cell 16, wherein cathode 20 begins to produce ions through an electrochemical reaction. These ions are then driven across membrane 26 through the operation of device, into anode half-cell 22. As the ions pass across membrane 26, they bring with them small amounts of the fluid contained in cathode half-cell 18, increasing the total volume contained within anode half-cell 22. As the volume of fluid in anode half-cell 22 increases, piston 28 is pushed into drug reservoir 30, compressing lining 32 as well as the medicament contained therein. Thereafter, the medicament is pushed out through exit port 36, delivering the medicament to the surrounding environment.

As an alternative to filling cell 16 via fluid inlet 14, cell 16 may be pre-filled with fluid. Typically, such fluids include aqueous electrolytes and aqueous solutions that replicate bodily fluids in some fashion. Such fluids, as an example, may include isotonic saline, Ringer's solution, artificial dialysis fluid, and the like.

Once the ions are contained within anode half-cell 22, anode 24 acts to neutralize the ions. Anode 24 serves as a means for maintaining substantially constant salt concentration, and neutralizes ions in one of three ways: (1) through a complexation reaction with an ion produced by anode 24, (2) by catalyzing a self-complexation reaction for the anode. Cathode 20 and anode 24 may compromise identical materials, such as Ag/AgCl, so that an ion produced at the cathode 20 (such as a chloride ion) can then be recomplexed at the anode 24 (for example, with silver), neutralizing the free ion (through complexation and precipitation of AgCl).

An alternative embodiment of the present invention is shown in FIG. 3. In that embodiment, the electro osmotic cell 16 of the present invention is shown as comprising a cathode 20 and a first 24' and a second 24" anode. Battery output may be directed between first 24' and second 24" anode using switch 25 (See FIG. 4). Cathode 20 and first anode 24' comprise the substantially the same active materials, as discussed above. Second anode 24" comprises a different, but electrochemically compatible material. For example, second anode 24" could comprise Zn, Mg, Al or other suitable anode materials. Preferably, second anode 24" generates a soluble cation. Preferably, cathode 20 and first 24' and second 24" anode are each in electrical communication with controlling means 40', 40", and switch 42', 42", and first anode 24' is also in communication with power source 44. Alternatively, as shown in FIG. 4, if switch 25 is included, both first anode 24' and second anode 24" may be connected to power source 44.

Depending on the volume of second half cell 22, long term cell operation may lead to an operationally significant decrease in the electrolyte concentration in half cell 22. This decrease occurs because of the electro osmotic transport of water with the ions traversing membrane 26 without an increase in the amount of salt, due to the operation of anode 24'. By directing a portion of the current to second anode 24", soluble ions (cations) are generated and any concentration decrease can be offset.

In this embodiment, the operation of device 10 can be maximized through either the simultaneous use of, or alternating use of, a standard anode as second anode 24", and an anode 24' comprised of substantially the same active material as in cathode 20. Controlling means 40 can maximize the operation of device 10 by utilizing a flow directing means, which directs the electrical connection and operation of first 24' and second 24" anodes, as needed. To further that operation, controlling means 40 is placed in electrical communication with ionic sensor 46, which monitors the concentration of ions in anode half-cell 22. Once placed in electrical communication with the electrodes, controlling means 40 is capable of using either a cycling means, or a splitting means, to direct the flow of current to either first anode 24' or second anode 24", or both simultaneously. The timing and/or ratio of current flow to the anodes 24', 24" is additionally directed by controlling means 40.

To maximize operation of device 10 having anode 24' and second anode 24" in operation together, as shown in FIG. 3, device may include first wiring loop 50 connecting cathode 20 to anode 24', and second wiring loop 52 connecting cathode 20 to second anode 24". In such an operational setup, each loop 50, 52 includes switch 42', 42", and controlling means 40', 40". First wiring loop 50 additionally includes power source 44 for conducting cell operations as described above. Generally, such a configuration should allow for independent operation of each of anode 24' and second anode 24".

In certain environments, however, anode 24' may interfere with the operations of second anode 24", and vice versa. In order to help prevent such interference, it is preferable that controlling means 40', 40" comprise a standard resistor, and that controlling means 40" has a much larger resistance than controlling means 40'. For example, controlling means 40" could provide a resistance ten times greater than the resistance of controlling means 40'. By increasing the resistance in second wiring loop 52, current flow can be decreased within that loop, and, in turn, the deleterious effect of second anode 24" on anode 24' can be reduced.

The foregoing description merely explains and illustrates the invention and the invention is not limited thereto except insofar as the appended claims are so limited, as those skilled in the art that have the disclosure before them will be able to make modifications without departing from the scope of the invention.

What is claimed is:

1. An electro-osmotic cell for use in a fluid delivery system, comprising:
a cell housing having a first half cell and a second half cell, with an ion selective membrane therebetween;
a first electrode positioned within the first half cell;
a second electrode positioned within the second half cell, said second electrode comprising silver for reacting with an ion passing through said ion selective membrane to form an insoluble product;
an electrolyte in electrical communication with both the first electrode and the second electrode; and
means for maintaining a substantially constant salt concentration within the electrochemical cell during operation of same.

2. The electrochemical cell according to claim 1, wherein the maintaining means comprises means for creating a chemical reaction with an ion, passed through the ion-selective membrane, so as to neutralize that ion.

3. The electrochemical cell according to claim 2, wherein the creating means results in a substantially insoluble product.

4. The electrochemical cell according to claim 2, wherein the creating means at least partially results in water as a product.

5. The electrochemical cell according to claim 1, wherein the maintaining means comprises the first electrode and the second electrode being fabricated from a common active material.

6. The electrochemical cell according to claim 5, wherein the active material of the first and second electrodes comprises silver/silver chloride.

7. The invention according to claim 1, wherein the electrochemical cell additionally comprises means for controlling the operation of the electrochemical cell, wherein the controlling means is capable of regulating at least one of the magnitude and time course of current flow within the electrochemical cell.

8. The invention according to claim 7, wherein the electrochemical cell comprises at least two second electrodes, and the controlling means comprises means for directing the flow of current between the first electrode and the at least two second electrodes.

9. The electrochemical cell according to claim 8, wherein the flow directing means comprises means for cycling current flow between the at least two second electrodes.

10. The electrochemical cell according to claim 8, wherein the flow directing means comprises means for splitting the current flow between the at least two second electrodes.

11. The invention according to claim 1, wherein the electrochemical cell additionally comprises a sensor associated with the cell for determining the ionic concentration of at least one of the first half cell and the second half cell.

12. The invention according to claim 1, wherein the electrolyte comprises water as an electrolyte solvent.

13. The invention according to claim 1, wherein the electrolyte replicates to some extent a bodily fluid.

14. An electro-osmotic delivery device, comprising:
a fluid inlet;
an electro-osmotic cell in fluid communication with the fluid inlet;
a movable barrier adjacent the electrochemical cell; and
a drug reservoir adjacent a piston member, the drug reservoir comprising an exit port;
wherein the electro-osmotic cell comprises:
a cell housing having a first half cell and a second half cell, with an ion selective membrane therebetween;
a first electrode positioned within the first half cell;
a second electrode positioned within the second half cell, said second electrode comprising silver for reacting with an ion passing through said ion selective membrane to form an insoluble product;
an electrolyte in electrical communication with both the first electrode and the second electrode; and
means for maintaining a substantially constant salt concentration within the electrochemical cell during operation of same.

15. The delivery device according to claim 14, wherein the maintaining means comprises means for creating a chemical reaction with an ion, passed through the ion-selective membrane, so as to neutralize that ion.

16. The electrochemical cell according to claim 15, wherein the creating means results in a substantially insoluble product.

17. The electrochemical cell according to claim 15, wherein the creating means at least partially results in water as a product.

18. The delivery device according to claim 14, wherein the maintaining means comprises the first electrode and the second electrode being fabricated from a common active material.

19. The delivery device according to claim 18, wherein the active material of the first and second electrodes comprises silver/silver chloride.

20. The invention according to claim 14, wherein the electrochemical cell additionally comprises means for controlling the operation of the electrochemical cell, wherein the controlling means is capable of regulating at least one of the magnitude and time course of current flow within the electrochemical cell.

21. The invention according to claim 20, wherein the electrochemical cell comprises at least two second electrodes, and the controlling means comprises means for directing the flow of current between the first electrode and the at least two second electrodes.

22. The delivery device according to claim 21, wherein the flow directing means comprises means for cycling current flow between the at least two second electrodes.

23. The delivery device according to claim 21, wherein the flow directing means comprises means for splitting the current flow between the at least two second electrodes.

24. The delivery device according to claim 14, wherein the electrochemical cell additionally comprises a sensor associated with the cell for determining the ionic concentration of at least one of the first half cell and the second half cell.

25. The delivery device according to claim 14, wherein the fluid inlet comprises a porous structure.

26. The delivery device according to claim 14, wherein the fluid inlet comprises a semi-permeable structure.

27. The delivery device according to claim 26, wherein the semi-permeable structure is permeable to water, but substantially impermeable to ions.

28. The invention according to claim 14, wherein the electrolyte comprises water as an electrolyte solvent.

29. The invention according to claim 14, wherein the electrolyte replicates to some extent a bodily fluid.

30. A method for delivering medicament or other beneficial agent to an animal, including a human, consisting of constructing the electro-osmotic delivery device of claim 11, filling it with a medicament/beneficial agent formulation, implanting and activating the device for delivery of the medicament/beneficial agent formulation at a controlled rate.

31. An electro-osmotic delivery device, comprising:
a fluid inlet;
an electro-osmotic cell in fluid communication with the fluid inlet;
a movable barrier adjacent the electrochemical cell; and a drug reservoir adjacent a piston member, the drug reservoir comprising an exit port;
wherein the electro-osmotic cell comprises:
a cell housing having a first half cell and a second half cell, with an ion selective membrane therebetween;
a first electrode positioned within the first half cell;
a second electrode positioned within the second half cell;
an electrolyte in electrical communication with both the first electrode and the second electrode;
and means for maintaining a substantially constant salt concentration within the electrochemical cell during operation of same, said means comprising an ionic sensor within the cell housing for measuring the ionic concentration of at least one of the two half cells.

32. An electro-osmotic cell for use in a fluid delivery system, comprising:
a cell housing having a first half cell and a second half cell, with an ion selective membrane therebetween;
a first electrode positioned within the first half cell;
a second electrode positioned within the second half cell, said second electrode comprising silver for reacting with an ion passing through said ion selective membrane;
an electrolyte in electrical communication with both the first electrode and the second electrode; and
means for creating a chemical reaction with a chloride ion passed through the ion-selective membrane, resulting in a insoluble product.

33. The electrochemical cell according to claim 32, wherein the first electrode and the second electrode are fabricated from a common active material.

34. The electrochemical cell according to claim 33, wherein the active material of the first and second electrodes comprises silver/silver chloride.

35. The invention according to claim 33, wherein the electrochemical cell additionally comprises means for controlling the operation of the electrochemical cell, wherein the controlling means is capable of regulating at least one of the magnitude and time course of current flow within the electrochemical cell.

36. The invention according to claim 33, wherein the electrochemical cell additionally comprises a sensor associated with the cell for determining the ionic concentration of at least one of the first half cell and the second half cell.

* * * * *